United States Patent [19]

Su

[11] Patent Number: 5,834,450
[45] Date of Patent: Nov. 10, 1998

[54] 9-(SUBSTITUTED AMINO)-ALPHA-6-DEOXY-5-OXY TETRACYCLINE DERIVATIVES, THEIR PREPARATION AND THEIR USE AS ANTIBIOTICS

[75] Inventor: Wei-guo Su, New London, Conn.

[73] Assignee: Pfizer Inc., New York, N.Y.

[21] Appl. No.: 682,640

[22] PCT Filed: Jan. 12, 1995

[86] PCT No.: PCT/IB95/00026

§ 371 Date: Jul. 22, 1996

§ 102(e) Date: Jul. 22, 1996

[87] PCT Pub. No.: WO95/22529

PCT Pub. Date: Aug. 24, 1995

[51] Int. Cl.$^6$ .......................... A01N 37/18; C07C 237/26
[52] U.S. Cl. .......................... 514/152; 514/445; 552/204; 552/205; 549/65
[58] Field of Search ................ 549/65; 552/204, 552/205; 514/445, 152

[56] References Cited

U.S. PATENT DOCUMENTS 5,371,076  12/1994  Lee et al. ................................ 514/152

*Primary Examiner*—Deborah C. Lambkin
*Attorney, Agent, or Firm*—P. C. Richardson; P. H. Ginsburg; Jolene W. Appleman

[57] ABSTRACT

This invention relates to compounds of the formula

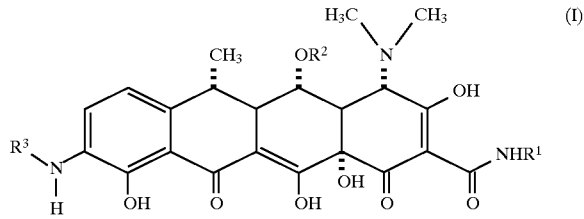

wherein $R^1$, $R^2$ and $R^3$ are defined as in the specification and the pharmaceutically acceptable salts of such compounds. Compounds of the formula I exhibit antibiotic activity against a wide range of gram-positive and gram-negative organisms, including organisms that are resistant to tetracycline antibiotics.

8 Claims, No Drawings

9-(SUBSTITUTED AMINO)-ALPHA-6-DEOXY-5-OXY TETRACYCLINE DERIVATIVES, THEIR PREPARATION AND THEIR USE AS ANTIBIOTICS

This application is a 371 of PCT/IB95/00026 filed Jan. 12, 1995.

This invention relates to novel doxyline analogs that exhibit antibiotic activity against a wide range of gram-positive and gram-negative organisms, including organisms that are resistant to tetracycline antiobiotics.

Doxycycline (α-6-deoxy-5-oxytetracycline) and other 6-deoxytetracyclines are referred to in articles by Stephens et al., *J. Amer. Chem. Soc.*, 85, 2643–2652 (Sep. 5, 1963) and Petisi et al., *J. Med. Pharm. Chem.*, 5 538 (1962). They are also referred to in U.S. Pat. No. 3,200,149, which issued on Aug. 10, 1965.

European Patent Application 536515A1, which was published on Apr. 14, 1993, refers to 7-substituted-9-(substituted amino)6-demethyl-6-deoxytetracycline compounds that exhibit activity against a wide spectrum of organisms including organisms that are resistant to tetracyclines. This application and the foregoing references are incorporated herein by reference in their entireties.

SUMMARY OF THE INVENTION

This invention relates to compounds of the formula

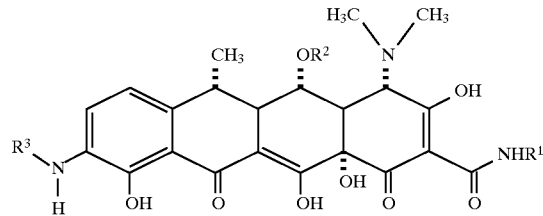

wherein $R^1$ is hydrogen or —$CH_2NR^5R^6$;
$R^2$ is hydrogen or $R^4(CH_2)_nCO$—;
n is an integer from 0 to 4;
$R^3$ is $R^8(CH_2)_mCO$— or $R^8(CH_2)_mSO_2$—;
m is an integer from 0 to 4;
and when n is 0, then either:

(a) $R^4$ is selected from hydrogen; amino; monosubstituted amino selected from straight or branched ($C_1$–$C_6$) alkylamino, cyclopropylamino, cyclobutylamino, benzylamino and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-(1,2,4-triazolyl); straight or branched ($C_1$–$C_4$)alkyl selected from methyl, ethyl, n-propyl, 1-methylethyl, n-butyl, 1-methylpropyl, 2-methylpropyl and 1,1-dimethylethyl; ($C_3$–$C_6$)cycloalkyl selected from cyclopropyl, cyclobutyl, cyclopentyl and cyclohexyl; substituted ($C_3$–$C_6$)cycloalkyl (substitution selected from ($C_1$–$C_3$)alkyl, cyano, amino and ($C_1$–$C_3$)acyl); ($C_6$–$C_{10}$)aryl selected from phenyl, α-naphthyl and β-naphthyl; substituted ($C_6$–$C_{10}$)aryl (substitution selected from halo, ($C_1$–$C_4$)alkoxy, trihalo ($C_1$–$C_3$)alkyl, nitro, amino, cyano, ($C_1$–$C_4$)alkoxycarbonyl, ($C_1$–$C_3$)alkylamino and carboxy); ($C_7$–$C_9$)aralkyl selected from benzyl, 1-phenylethyl, 2-phenylethyl and phenylpropyl; α-amino-($C_1$–$C_4$)alkyl selected from aminomethyl, α-aminoethyl, α-aminopropyl and α-aminobutyl; carboxy ($C_2$–$C_4$)-alkylamino selected from aminoacetic acid, α-aminobutyric acid and α-aminopropionic acid and their optical isomers; ($C_7$–$C_9$)aralkylamino (e.g., phenylglycyl); ($C_1$–$C_4$)alkoxycarbonylamino substituted ($C_1$–$C_4$)alkyl, substitution selected from phenyl and p-hydroxyphenyl; α-hydroxy($C_1$–$C_3$)alkyl selected from hydroxymethyl, α-hydroxyethyl, α-hydroxy-1-methylethyl and α-hydroxypropyl; α-mercaptopropyl; and halo-($C_1$–$C_3$) alkyl; or (b) $R^4$ is selected from $Q^1$, $Q^2$ and $Q^3$, wherein $Q^1$ is a five membered aromatic or saturated ring containing one N, O, S or Se heteroatom optionally having a benzo or pyrido ring fused thereto (e.g.,

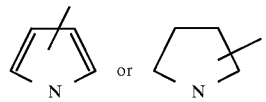

wherein Z is N, O, S or Se);

$Q^2$ is a five membered aromatic ring containing two heteroatoms independently selected from N, O, S and Se and optionally having a benzo or pyrido ring fused hereto (e.g.,

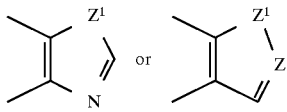

wherein Z and $Z^1$ are independently selected from N, O, S and Se); and $Q^3$ is a five membered saturated ring containing one or two heteroatoms independently selected from N, O, S and Se and an adjacent appended O heteroatom (for example,

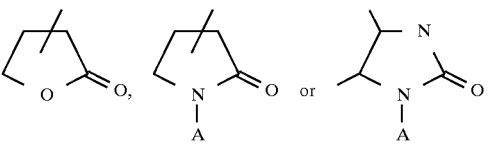

wherein A is selected from hydrogen; straight or branched ($C_1$–$C_4$)alkyl; $C_6$-aryl; substituted $C_6$-aryl (substitution selection from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$) alkylamino and carboxy); ($C_7$–$C_9$)aralkyl group selected from benzyl, 1-phenylethyl, 2-phenylethyl and phenylpropyl); or (c) $R^4$ is a six membered aromatic ring containing from one to three heteroatoms independently selected from N, O, S and Se (e.g., pyridyl, pyridazinyl, pyrazinyl, sym-triazinyl, unsym-triazinyl, pyrimidinyl or ($C_{1-3}$) alkylthiopyridazinyl), or a six membered saturated ring containing one or two heteroatoms independently selected from N, O, S and Se and an adjacent appended O heteroatom (e.g., 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholino and 2-dioxothiomorpholino); or (d) $R^4$ is selected from acetyl, propionyl; chloroacetyl; trifluoroacetyl; ($C_3$–$C_6$)cycloalkylcarbonyl (e.g., cyclopropylcarbonyl, cyclobutylcarbonyl, cyclopentylcarbonyl, cyclohexylcarbonyl, (2,2-dimethylcyclopropyl)carbonyl, (1,2-dimethylcyclopropylcarbonyl, (2-ethylcyclopropyl) carbonyl, (2-methylcyclopropyl) carbonyl or (3-ethylcyclobutyl)carbonyl); ($C_1$–$C_{10}$)aroyl selected from benzoyl and naphthoyl; halo substituted ($C_6$–$C_{10}$)aroyl (e.g., pentafluorobenzoyl, 4-chlorobenzoyl, 3-bromobenzoyl or 3,4-difluorobenzoyl); $(C_1-C_4)$alkylbenzoyl; and (heterocycle)carbonyl, wherein said heterocycle is selected from the group consisting of $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (e) $R^4$ is selected from $(C_1-C_4)$alkoxycarbonyl selected from methoxycarbonyl, ethoxycarbonyl, straight or branched propoxylcarbonyl, straight or branched butoxycarbonyl and allyloxycarbonyl; vinyl; and substituted vinyl [substitution selected from $(C_1-C_3)$alkyl, halo, $(C_6-C_{10})$aryl selected from phenyl, α-naphthyl and β-naphthyl, substituted $(C_6-C_{10})$aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy), halo $(C_1-C_3)$alkyl, and $Q^1$, wherein $Q^1$ is defined as above]; or (f) $R^4$ is selected from $(C_1-C_4)$alkoxy; $C_6$-aryloxy selected from phenoxy and substituted phenoxy (substitution selected from halo, $(C_1-C_4)$alkyl, nitro, cyano, thiol, amino, carboxy and di$(C_1-C_3)$alkylamino); $(C_7-C_{10})$ aralkyloxy (e.g., benzyloxy, 1-phenylethyloxy or 2-phenylethyloxy); vinyloxy and substituted vinyloxy (substitution selected from $(C_1-C_4)$alkyl, cyano, carboxy, and $(C_6-C_{10})$aryl selected from phenyl, α-naphthyl and β-naphthyl); $R^aR^b$ amino$(C_1-C_4)$alkoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$ wherein p is 2–6, or $R^aR^b$ is —$(CH_2)_2W(CH_2)_2$— wherein W is selected from —N$(C_1-C_3)$alkyl (straight or branched), —NH, —NOB (wherein B is selected from hydrogen and $(C_1-C_3)$alkyl), O and S; and $R^aR^b$aminoxy, wherein $R^aR^b$ is a straight or branched $(C_1-C_4)$alkyl selected from methyl, ethyl, n-propyl, 1-methylethyl, n-butyl, 1-methylpropyl, 2-methylpropyl, and 1,1-dimethylethyl, or $R^aR^b$ is $(CH_2)_p$ wherein p is 2–6, or $R^aR^b$ is —$(CH_2)_2W(CH_2)_2$— wherein W is selected from —N$(C_1-C_3)$alkyl (straight or branched), —NH, —NOB (wherein B is selected from hydrogen and $(C_1-C_3)$alkyl), O and S;

and when n is 1, 2, 3 or 4, then either:

(a) $R^4$ is selected from hydrogen; amino; straight or branched $(C_1-C_4)$alkyl selected from methyl, ethyl, n-propyl, 1-methylethyl, n-butyl, 1-methylpropyl, 2-methylpropyl and 1,1-dimethylethyl; $(C_3-C_6)$cycloalkyl selected from cyclopropyl, cyclobutyl, cyclopentyl and cyclohexyl; substituted $(C_3-C_6)$cycloalkyl group (substitution selected from $(C_1-C_3)$alkyl, cyano, amino and $(C_1-C_3)$acyl); $(C_6-C_{10})$aryl selected from phenyl, α-naphthyl and β-naphthyl; substituted $(C_6-C_{10})$aryl (substitution selected from halo, $(C_1-C_4)$alkoxy, trihalo $(C_1-C_3)$alkyl, nitro, amino, cyano, $(C_1-C_4)$alkoxycarbonyl, $(C_1-C_3)$alkylamino and carboxy); $(C_7-C_9)$aralkyl (e.g., benzyl, 1-phenylethyl, 2-phenylethyl or phenylpropyl); acetyl; propionyl; chloroacetyl; trichloroacetyl; $(C_6-C_{10})$ aroyl selected from benzoyl and naphthoyl; halo substituted $(C_6-C_{10})$aroyl (e.g., pentafluorobenzoyl, 4-chlorobenzoyl, 3-bromobenzoyl and 3,4-difluorobenzoyl); $(C_{1-4})$ alkylbenzoyl (e.g., 4-toluoyl, 2-toluoyl or 4-(1-methylethyl) benzoyl); $(C_3-C_6)$cycloalkylcarbonyl; and (heterocycle) carbonyl, wherein the heterocycle moiety is selected from the group consisting of $Q^1$, $Q^2$, $Q^3$, six membered aromatic rings containing from one to three heteroatoms independently selected from N, O S and Se, and six membered saturated rings containing one or two heteroatoms independently selected from N, O, S and Se and an adjacent appended O heteroatom, wherein $Q^1$, $Q^2$ and $Q^3$ are defined as above; or (b) $R^4$ is selected from $(C_1-C_4)$alkoxy; $C_6$-aryloxy selected from phenoxy and substituted phenoxy (substitution selected from halo, $(C_1-C_4)$alkyl, nitro, cyano, thiol, amino, carboxy and di$(C_1-C_3)$alkylamino); $(C_7-C_{10})$ aralkyloxy (e.g., benzyloxy, 1-phenylethyloxy or 2-phenylethyloxy); $(C_1-C_3)$alkylthio selected from methylthio, ethylthio, propylthio and allylthio; $C_6$-arylthio selected from phenylthio and substituted phenylthio (substitution selected from halo, $(C_1-C_4)$alkyl, nitro, cyano, thiol, amino, carboxy and di$(C_1-C_3)$alkylamino); $C_6$-arylsulfonyl selected from phenylsulfonyl and substituted phenylsulfonyl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy); and $(C_7-C_8)$aralkylthio (e.g., benzylthio, 1-phenylethylthio or 2-phenylethylthio); or (c) $R^4$ is selected from $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (d) $R^4$ is selected from hydroxy; mercapto; mono- or di-straight or branched chain $(C_1-C_6)$alkylamino selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl and 1-methyl-1-ethylpropyl amino; $(C_2-C_5)$ azacycloalkyl (e.g., aziridinyl, azetidinyl, pyrrolidinyl, piperidinyl, morpholino or 2-methylpyrrolidinyl); carboxy $(C_2-C_4)$alkylamino selected from aminoacetic acid, α-aminopropionic acid, α-aminobutyric acid and their optical isomers; α-hydroxy$(C_1-C_3)$alkyl selected from hydroxymethyl, α-hydroxyethyl, α-hydroxy-1-methylethyl and α-hydroxypropyl; halo$(C_1-C_3)$ alkyl; acetyl; propionyl; chloroacetyl; trifluoroacetyl; $(C_6-C_{10})$aroyl selected from benzoyl and naphthoyl; halo substituted $(C_6-C_{10})$aroyl (e.g., pentafluorobenzoyl, 4-chlorobenzoyl, 3-bromobenzoyl, or 3,4-difluorobenzoyl); $(C_1-C_4)$alkylbenzoyl; (e.g., 4-toluoyl, 2-toluoyl or 4-(1-methylethyl)benzoyl); $(C_3-C_6)$ cycloalkylcarbonyl; and (heterocycle)carbonyl, wherein the heterocycle moiety is selected from $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (e) $R^4$ is selected from $(C_{1-4})$alkoxycarbonylamino selected from tert-butoxycarbonylamino, allyloxycarbonylamino, methoxycarbonylamino, ethoxycarbonylamino and propoxycarbonylamino; $(C_1-C_4)$ alkoxycarbonyl selected from methoxycarbonyl, ethoxycarbonyl, straight or branched propoxycarbonyl, and straight or branched butoxycarbonyl; allyloxycarbonyl; $R^aR^b$amino$(C_1-C_4)$alkoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W(CH_2)_2$— wherein W is selected from —N$(C_1-C_3)$alkyl (straight or branched), —NH, —NOB (wherein B is selected from hydrogen and $(C_1-C_3)$alkyl), O and S; and $R^aR^b$aminoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W(CH_2)_2$— wherein W is selected from —N$(C_1-C_3)$alkyl (straight or branched), —NH, —NOB (wherein B is selected from hydrogen and $(C_1-C_3)$alkyl), O and S;

and when $R^3$ is $R^8(CH_2)_mCO$ and m is 0, then $R^8$ is independently selected from the same group of substituents that $R^4$ is selected from when n is 0;

and when $R^3$ is $R^8(CH_2)_mCO$ and m is 1, 2, 3 or 4, then $R_8$ is independently selected from the same group of substitutents that $R^4$ is selected from when n is 1, 2, 3 or 4;

and when $R^3$ is $R^8(CH_2)_mSO_2$ and m is 0, then either:

(a) $R^8$ is selected from amino; monosubstituted amino selected from straight or branched $(C_1-C_6)$-alkylamino, cyclopylamino, cyclobutylamino, benzylamino and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-(1,2,4-triazolyl); straight or branched $(C_1-C_4)$alkyl selected from methyl, ethyl, n-propyl, 1-methylethyl, n-butyl, 1-methylpropyl, 2-methylpropyl and 1,1-dimethylethyl; $(C_3-C_6)$cycloalkyl selected from cyclopropyl, cyclobutyl, cyclopentyl and cyclohexyl; substituted $(C_3-C_6)$cycloalkyl (substitution selected from $(C_1-C_3)$alkyl, cyano, amino and $(C_1-C_3)$acyl); $(C_6-C_{10})$aryl selected from phenyl, α-naphthyl and β-naphthyl; substituted $(C_6-C_{10})$aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy); $(C_7-C_9)$aralkyl (e.g., benzyl, 1-phenylethyl, 2-phenylethyl or phenylpropyl); and halo$(C_1-C_3)$alkyl; or (b) $R^8$ is a heterocycle group selected from $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; $R^aR^b$amino$(C_1-C4)$alkoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W$—$(CH_2)_2$—, wherein W is selected from —N$(C_1-C_3)$alkyl (straight or branched), —NH, —NOB (wherein B is selected from hydrogen and $(C_1-C_3)$alkyl), O and S; and $R^aR^b$ aminoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W(CH_2)_2$— wherein W is selected from —N$(C_1-C_3)$alkyl (straight or branched), —NH, —NOB (wherein B is selected from hydrogen or $(C_1-C_3)$alkyl), O and S, wherein $Q^1$, $Q^2$ and Q3 are defined as above;

and when $R^3$ is $R^8 (CH_2)_mSO_2$ and m is 1, 2, 3, or 4, then either:

(a) $R^8$ is selected from hydrogen; straight or branched $(C_1-C_4)$alkyl selected from methyl, ethyl, n-propyl, 1-methylethyl, n-butyl, 1-methylpropyl, 2-methylpropyl and 1,1-dimethylethyl; $(C_1-C_4)$carboxyalkyl; $(C_3-C_6)$ cycloalkyl selected from cyclopropyl, cyclobutyl, cyclopentyl and cyclohexyl; substituted $(C_3-C_6)$cycloalkyl (substitution selected from $(C_1-C_3)$alkyl, cyano, amino and $(C_1-C_3)$acyl); $(C_6-C_{10})$aryl selected from phenyl, α-naphthyl and β-naphthyl; substituted $(C_6-C_{10})$aryl (substitution selected from halo, $(C_1-C_3)$alkoxy, trihalo $(C_1-C_3)$alkyl, nitro, amino, cyano, $(C_1-C_4)$alkoxycarbonyl, $(C_1-C_3)$alkylamino and carboxy); $(C_7-C_9)$aralkyl (e.g., benzyl, 1-phenylethyl, 2-phenylethyl or phenylpropyl); $(C_1-4)$alkoxy; $C_6$-aryloxy selected from phenoxy and substituted phenoxy (substitution selected from halo, $(C_{1-3})$ alkyl, nitro, cyano, thiol, amino, carboxy and di$(C_1-C_3)$ alkylamino); $(C_7-C_{10})$aralkyloxy (e.g., benzyloxy, 1-phenylethyloxy or 2-phenylethyloxy); $R^aR^b$amino $(C_1-C_4)$alkoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W(CH_2)_2$—, wherein W selected from —N$(C_{1-3})$alkyl (straight or branched), —NH, —NOB (wherein B is selected from hydrogen and $(C_1-C_3)$alkyl), O and S; and $R^aR^b$ aminoxy, wherein $R^aR^b$ is straight or branched $(C_1-4)$alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W(CH_2)_2$—, wherein W is selected from —N$(C_1-C_3)$alkyl (straight or branched), —NH, —NOB (wherein B is selected from hydrogen and $(C_1-C_3)$alkyl), O and S; or (b) $R^8$ is selected from $(C_1-C_3)$alkylthio selected from methylthio, ethylthio and n-propylthio; $C_6$-arylthio selected from phenylthio and substituted phenylthio (substitution selected from halo, $(C_1-C_3)$alkyl, nitro, cyano, thiol, amino, carboxy and di$(C_1-C_3)$alkylamino); $(C_7-C_8)$aralkylthio (e.g., benzylthio, 1-phenylethylthio or 2-phenylethylthio); and heterocycle groups selected from the group consisting of $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (c) $R^8$ is selected from hydroxy; mercapto; mono- or di-straight or branched $(C_1-C_6)$alkylamino group selected from methyl, ethyl, n-propyl, 1-methylethyl, n-butyl, 1-methylpropyl, 2-methylpropyl, 1,1-dimethylethyl, 2-methylbutyl, 1,1,-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl and 1-methyl-1-ethylpropyl amino; halo $(C_1-C_3)$alkyl; acetyl; propionyl; chloroacetyl; trifluoroacetyl; $(C_6-C_{10})$aroyl selected from benzoyl and naphthoyl; halo substituted $(C_6-C_{10})$aroyl (e.g., pentafluorobenzoyl, 4-chlorobenzoyl, 3-bromobenzoyl or 3,4-difluorobenzoyl); $(C_1-C_4)$alkylbenzoyl (e.g., 4-toluoyl, 2-toluoyl or 4-(1-methylethyl)benzoyl); $(C_3-C_6)$cycloalkylcarbonyl; and (heterocycle)carbonyl, wherein the heterocycle moiety is selected from $Q^1$, $Q^2$, $Q^3$, six membered aromatic rings containing one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (d) $R^8$ is selected from $(C_1-4)$alkoxycarbonyl selected from methoxycarbonyl, ethoxycarbonyl, straight or branched propoxycarbonyl, allyloxycarbonyl and straight or branched butoxycarbonyl; and $R^5$ and $R^6$ are independently selected from hydrogen; straight or branched $(C_1-C_3)$alkyl selected from methyl, ethyl, n-propyl and 1-methylethyl; $(C_6-C_{10})$aryl selected from phenyl, α-naphthyl and β-naphthyl; $(C_7-C_9)$aralkyl (e.g., benzyl, 1-phenylethyl, 2-phenylethyl or phenylpropyl); heterocycles selected from the group consisting of $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom; —$(CH_2)_k COOR^7$ where k is 0–4 and $R^7$ is selected from hydrogen and straight or branched $(C_1-C_3)$alkyl selected from methyl, ethyl, n-propyl and 1-methylethyl; and $(C_6-C_{10})$aryl selected from phenyl, α-naphthyl and β-naphthyl, wherein $Q^1$, $Q^2$ and $Q^3$ are defined as above;

or $R^5$ and $R^6$, taken together, are —$(CH_2)_2 W(CH_2)_2$—, wherein W is selected from $(CH_2)_q$ wherein q is 0–1, —NH, —N$(C_1-C_3)$alkyl (straight or branched), —N$(C_1-C_4)$ alkoxy, oxygen, sulfur and substituted congeners selected from (L or D)proline, ethyl(L or D)prolinate, morpholine, pyrrolidine and piperidine;

with the proviso that: (a) $R^5$ and $R^6$ cannot both be hydrogen.

The compounds of formula I that are basic in nature are capable of forming a wide variety of salts with various inorganic and organic acids. The acids that may be used to prepare pharmaceutically acceptable acid addition salts of those compounds of formula I that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

The compounds of formula I that are acidic in nature are capable of forming a wide variety of base salts. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

This invention also relates to the pharmaceutically acceptable acid addition and base salts of compounds of the formula I.

A preferred embodiment of this invention relates to compounds of the formula I wherein $R^2$ is $(C_{1-6})$alkyl-(C=O)—, phenyl-(C=O)— or phenylmethyl-(C=O)—.

Another preferred embodiment of the invention relates to compounds of the formula I wherein $R^3$ is —(C=O)—$CH_2$—$N(CH_3)_2$.

Another preferred embodiment of this invention relates to compounds of the formula I wherein $R^3$ is —(C=O)—$CH_2$—$N(CH_3)_2$ and $R^1$ is hydrogen.

Examples of specific embodiments of this invention are the following compounds and their pharmaceutically acceptable salts:

9-dimethylaminoacetylamino-6α-deoxy-5-oxy-tetracycline;

9-dimethylaminoacetylamino-6α-deoxy-5-formyloxy-tetracycline;

9-dimethylaminoacetylamino-6α-deoxy-5-acetoxy-tetracycline;

9-dimethylaminoacetylamino-6α-deoxy-5-propionyloxy-tetracycline;

9--dimethylaminoacetylamino-6α-deoxy-5-phenylcarbonyloxy-tetracycline;

9-dimethylaminoacetylamino-6α-deoxy-5-benzylcarbonyloxy-tetracycline;

9-dimethylaminoacetylamino-6α-deoxy-5-aminocarbonyloxy-tetracycline;

9-dimethylaminoacetylamino-6αa-deoxy-5-dimethylaminoacetoxy-tetracycline;

9-dimethylaminoacetylamino-6α-deoxy-5-dimethylaminocarbonyloxy-tetracycline;

9-dimethylaminoacetylamino-6α-deoxy-5-cyclopentylcarbonyloxy-tetracycline;

9-dimethylaminoacetylamino-6α-deoxy-5-cyclohexycarbonyloxy-tetracycline; and 9-dimethylaminoacetylamino-6α-deoxy-5-pyridinocarbonyloxy-tetracycline.

Other embodiments of this invention include compounds of the formula I, and their pharmaceutically acceptable salts, wherein $R^3$ is selected from the group consisting of formyl, acetyl, methoxyacetyl, acetyloxyacetyl, benzoyl, 4-methoxybenzoyl, 2-methylbenzoyl, 2-fluorobenzoyl, pentafluorobenzoyl, 3-trifluoromethylbenzoyl, 2-furanylcarbonyl, 2-thienylcarbonyl, 4-aminobenzoyl, aminocarbonyl, phenylsulfonyl, 4-chlorophenylsulfonyl, 3-nitrophenylsulfonyl, 2-thienylsulfonyl, 3-nitrophenylsulfonyl, 2-thienylsulfonyl, methanesulfonyl, phenylmethoxyacetyl, hydroxyacetyl, methylaminoacetyl, dimethylaminoacetyl, 4-bromo-1-oxobutyl, (4-dimethylamino)benzoyl, aminoacetyl, ethylsulfonyl, chloroacetyl, bromoacetyl, 2-bromo-1-oxopropyl, cyclopropylaminoacetyl, (2-methylpropyl)aminoacetyl, (butylmethyl)aminoacetyl and (phenylmethyl)aminoacetyl.

Other embodiments of this invention include:

(a) compounds of the formula I wherein $R^2$ is other than hydrogen;

(b) compounds of the formula I wherein $R^2$ is other than hydrogen and $R^3$ is $R^8(CH_2)_m CO$—;

(c) compounds of the formula I wherein $R^3$ is $R^8(CH_2)_m SO_2$—;

(d) compounds of the formula I wherein $R^2$ is other than hydrogen and $R^3$ is —(C=O)—$CH_2$—$N(CH_3)_2$;

(e) compounds of the formula I wherein $R^1$ is hydrogen;

(f) compounds of the formula I wherein $R^1$ is hydrogen and $R^2$ is other than hydrogen;

(g) compounds of the formula I wherein $R^3$ is $R^8(CH_2)_m CO$—;

(h) compounds of the formula I wherein $R^3$ is $R^8(CH_2)_m CO$— and $R^8$ is other than amino or substituted amino;

(i) compounds of the formula I wherein $R^2$ is other than hydrogen, $R^3$ is $R^8(CH_2)_m CO$—, m is zero or one and $R^8$ is amino or substituted amino;

(j) compounds of the formula I wherein $R^2$ is hydrogen, $R^3$ is $R^8(CH_2)_m CO$—, m is zero or one and $R^8$ is other than amino or substituted amino; and (k) compounds of the formula I wherein $R^2$ is hydrogen, $R^3$ is $R^8(CH_2)_m CO$—, m is zero or one and $R^8$ is other than $(C_{1-6})$ alkylamino or di-$(C_1-C_6)$alkylamino.

Examples of possible $Q^1$ groups, as defined above for formula I, are the following: pyrrolyl, N-methylindolyl, 2-pyrrolidinyl, 3-pyrrolidinyl, 2-pyrrolinyl, tetrahydrofuranyl, furanyl, tetrahydrothienyl, thienyl, benzothienyl and selenazolyl.

Examples if possible $Q^2$ groups, as defined above for formula I, are the following: imidazolyl, pyrazolyl, benzimidazolyl, oxazolyl, benzoxazolyl, indazolyl thiazolyl, benzothiazolyl, 3-alkyl-3H-imidazo[4,5-b]pyridyl and pyridylimidazolyl.

Examples of possible $Q^3$ groups, as defined above for formula I, are γ-butyrolactam, γ-butyrolactone, immidazolidinone and N-aminoimidazolidinone.

Examples of "a six membered saturated ring containing one or two heteroatoms independently selected from N, O, S and Se and an adjacent appended O atom", as used above in the definition of $R^4$, are the following: 2,3-dioxo-1-piperazinyl, 4-ethyl-2,3-dioxo-1-piperazinyl, 4methyl-2,3-dioxo-1-piperazinyl, 4-cyclopropyl-2-dioxo-1-piperazinyl, 2-dioxomorpholino and 2-dioxothiomorpholino.

Examples of "a six membered aromatic ring containing from one to three heteroatoms independently selected from N, O, S and Se", as used above in the definition of $R^4$, are the following: pyridyl, pyridazinyl, pyrazinyl, sym-triazinyl, unsym-triazinyl, pyrimidinyl and $(C_1-C_3)$ alkylthiopyridazenyl.

The term "halo", as used herein, refers to chloro, bromo, fluoro and iodo.

The compounds of formula I have chiral centers and therefore exist in different and enantiomeric and diastereomeric forms. This invention relates to all optical isomers and all stereoisomers of compounds of the formula I, and mixtures thereof.

Formula I above also includes compounds identical to those depicted but for the fact that one or more hydrogens or carbon atoms are replaced by isotopes thereof. Such compounds are useful as research and diagnostic tools in metabolism pharmacokinetics studies and in binding assays.

This invention also relates to a pharmaceutical composition for treating or preventing a condition caused by a bacterial infection in a mammal, including a human, comprising an amount of a compound of the formula I, or pharmaceutically acceptable salt thereof, that is effective in treating or preventing such condition, and a pharmaceutical acceptable carrier.

The present invention also relates to a method of treating or preventing a condition caused by a bacterial infection in a mammal, including a human, comprising administering to said mammal an amount of a compound of the formula I, or pharmaceutically acceptable salt thereof, that is effective in treating or preventing such condition.

The present invention also relates to a pharmaceutical composition for treating or preventing a condition caused by a bacterial infection in a mammal, including a human, comprising an anti-bacterial effective amount of a compound of the formula I, or a pharmaceutical acceptable salt thereof, and a pharmaceutically acceptable carrier.

The present invention also relates to a method of treating or preventing a condition caused by a bacterial infection in a mammal, including a human, comprising an administering to said mammal an anti-bacterial effective amount of a compound of the formula I, or pharmaceutically acceptable salt thereof.

DETAILED DESCRIPTION OF THE INVENTION

Compounds of the formula I may be prepared as depicted in schemes 1–3 and described below. In the reaction schemes and discussion that follows, $R^1$, $R^2$, $R^3$, $R^4$, $R^5$ and $R^6$, unless otherwise indicated, are defined as above.

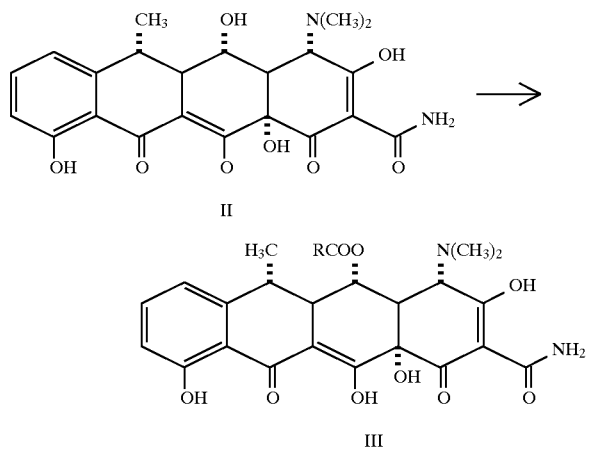

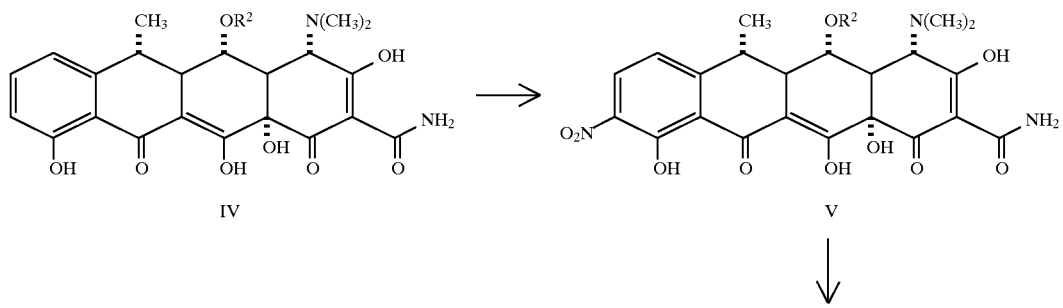

-continued
Scheme 2

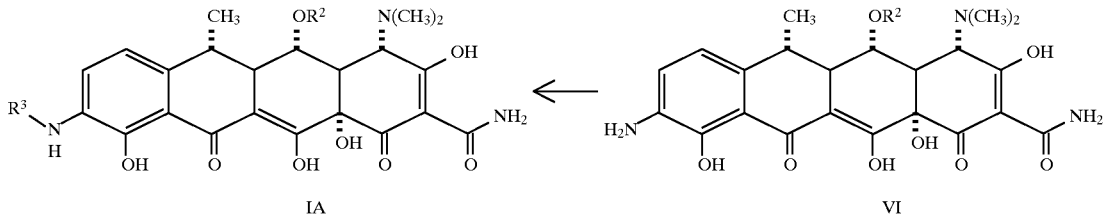

Scheme 3

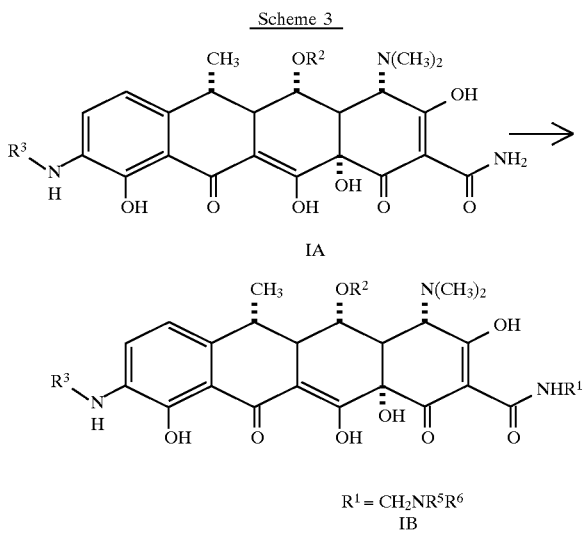

Referring to scheme 1, doxycycline (α-6-deoxy-5-oxytetracycline, structure II) is converted into the corresponding intermediate of formula III, wherein R is $R^4(CH_2)_n$—, by reacting it with a compound of the formula RCOOH, wherein R is defined as above, in methanesulfonic acid. This reaction is generally conducted at a temperature from about 0° C. to about 100° C., preferably from about 20° C. to about 50° C.

Scheme 2 illustrates the conversion compounds of the formula III and doxycycline, which are combined to form generic formula IV, into the corresponding compounds of the formula I wherein $R^1$ is hydrogen. Referring to scheme 2, compounds of the formula IV are first nitrated at position "9" by reaction with an alkali metal or alkaline earth metal nitrate in a strong acid (e.g., sulfuric, hydrofluoric or methanesulfonic acid). Suitable temperatures for this reaction range from about 0° C. to about 25° C., with about 0° C. being preferred.

The above nitration reaction yields the corresponding compounds of the formula V. Reduction of the nitro group at position "9" of these compounds yields the corresponding amino derivatives of the formula VI. The reduction is usually accomplished by hydrogenation in the presence of a metal containing catalyst. Suitable hydrogenation catalysts include palladium, platinium, nickel, platinium oxide and rhodium. The reaction temperature may range from about 10° C. to about 50° C., with about 25° C. being preferred. The hydrogenation is generally carried out at a pressure from about 1 to about 4 atmospheres, preferably from about 1.5 to 3 atmospheres, in a suitable inert solvent such as a lower alcohol or acetic acid.

The resulting compounds of the formula VI can be converted into the corresponding compounds of the formula I wherein $R^1$ is hydrogen (hereinafter referred to as compounds of the formula IA) by reacting them with a compound of the formula $R^3X$, wherein X is an appropriate leaving group (e.g., chloro, bromo, iodo, mesylate or tosylate) in the presence of a base. Suitable bases include alkali metal and alkaline earth metal carbonates. This reaction is generally conducted in a polar aprotic solvent such as 1,3-dimethyl-3,4,5,6-tetrahydro-2(1H)-pyrimidinone (DMPU), acetonitrile or dimethylformamide (DMF), preferably DMPU, at a temperature from about 0° C. to about 80° C., preferably at about room temperature.

Compounds of the formula IA can be converted into the corresponding compounds of the formula I wherein $R^1$ is $CH_2NR^5R^6$ (hereinafter referred to as compounds of the formula IB) by reacting them with a compound of the formula $NHR^5R^6$ and formaldehyde. This reaction is typically carried out in a polar solvent such as dimethylformamide (DMF) or a lower alcohol, preferably methoxyethanol, at a temperature from about 0° C. to about 100° C., preferably at about 55° C.

The compounds of formula I that are basic in nature are capable of forming a wide variety of salts with various inorganic and organic acids. The acids that may be used to prepare pharmaceutically acceptable acid addition salts of those compounds of formula I that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Although such salts must be pharmaceutically acceptable for administration to mammals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of formula I that are acidic in nature are capable of forming a wide variety of base salts. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of compounds of the formulae I that are acidic in nature may be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired metal and the solution subsequently evaporated to dryness.

The preparation of other compounds of the formula I not specifically described in the foregoing experimental section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as antibiotics in mammals, including humans. They are active against a wide range of gram-positive and gram-negative bacterial strains, including organisms that are resistant to tetracycline antibiotics. The antibiotic activity of the compounds of formula I and their pharmaceutically acceptable salts may be determined using the in vitro standard broth dilution method described by Waitz, J. A., *National Commission for Clinical Laboratory Standards Document M7-A2*, vol. 10, no. 8, pp. 13–20, 2nd edition, Villanova, Pa. (1990).

The compounds of the formula I and the pharmaceutically acceptable salts thereof can be administered via either the oral, parenteral or topical routes. In general, these compounds are most desirably administered in dosages ranging from about 0.1 mg up to about 1 gram per day, although variations will necessarily occur depending upon the weight and condition of the subject being treated and the particular route of administration chosen. However, a dosage level that is in the range of about 20 mg to about 200 mg per day is most desirably employed. Variations may nevertheless occur depending upon the species of mammal being treated and its individual response to said medicament, as well as on the type of pharmaceutical formulation chosen and the time period and interval at which such administration is carried out. In some instances, dosage levels below the lower limit of the above range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The following examples are given by way of illustration and are not to be construed as limitations of this invention, many variations of which are possible.

EXAMPLE 1

9-Nitro Doxycycline Sulfate

9-Nitro-Doxycycline was prepared according to the known procedure (J. Med. and Pharm. Chem., 5,538 (1962)). Thus Doxycycline (889 mg, 2 mmol) was dissolved in concentrated sulfuric acid (25 ml) at 0° C. To it was added solid potassium nitrate (404 mg, 4 mmol). The resulting mixture stirred at 0° C. for 20 minutes before it was poured into 100 g of ice. The mixture stirred until all ice chips have melted. Extraction with butanol (4×20 ml portions), washing of butanol with water (2×10 ml), concentration to a small volume to give 9-nitro-doxycycline sulfate as a yellow solid.

EXAMPLE 2

9-Amino Doxycycline Dihydrochloride

Product of example 1 was dissolved in methanol (1 g/100 ml) and concentrated hydrochloric acid (1 g/2.3 ml). To it was added platinum oxide catalyst (10% by weight). The mixture was treated with hydrogen at 23° C. and 45 psi pressure for 2 hours. Filtration through Celite and concentration gave 9-amino doxycycline dihydrochloride as a yellow solid.

EXAMPLE 3

9-N,N-dimethylglycylamido-Doxycycline Dihydrochloride

9-Amino doxycycline dihydrochloride (490 mg, 0.92 mmol) was suspended into 1,3-dimethyl-3,4,5,6-tetrahydro-2(1H)-pyrimidinone (DMPU, 9 ml) and acetonitrile (3 ml). To it was added solid sodium carbonate (488 mg, 5 equiv). After stirring at room temperature for 15 minutes, solid N,N-dimethylglycyl chloride hydrochloride salt (218 mg, 1.5 equiv) was added in one portion. The resulting mixture stirred at room temperature for 45 minutes. The insoluble materials were filtered off through filter paper and the filtrate was added dropwise into a solution of methylene chloride (300 ml), ether (150 ml) and 2M hydrochloric acid (HCl) in methanol (8 ml). The resulting yellow solid was collected by filtration and washed with methylene chloride. The crude product thus obtained was dissolved in 0.1M HCl in methanol (10 ml) and to it was added activated carbon. After stirring for 10 minutes, the mixture was filtered and the filtrate was concentrated in vacuo to dryness. The solid product was dissolved in methanol (5 ml) and the solution was added dropwise into methylene chloride (400 ml). The resulting precipitate was collected by filtration and washed with methylene chloride. The product was dried under a stream of nitrogen for 2 hours and finally under vacuum at 55° C. for 24 hours to give 370 mg of the product (65%). $^1$H-NMR (250 MHz, DMSO-$d_6$): 8.10 (d, 1H), 6.95 (d, 1H), 6.00 (d, 1H), 4.59 (s, 1H), 4.20 (s, 2H), 2.86 (s, 3H), 2.79 (s, 3H), 1.50 (d, 3H). FAB-MS: 545 (M+H$^+$).

EXAMPLE 4

5-Acyloxy Doxycyclines

Acylation of Doxycycline at 5-position was carried out following the known procedure (II. Farmoc., 29, 902 (1974)). Thus doxycycline (1 g) was dissolved in methanesulfonic acid (5 ml) (or hydrofluoric acid) and treated with carboxylic acid (1 g) between 23 and 55° C. After the reaction was complete, the mixture was poured into cold ether. The precipitate was collected by filtration and washed with ether to give the doxycycline 5-ester.

I claim:
1. A compound of the formula

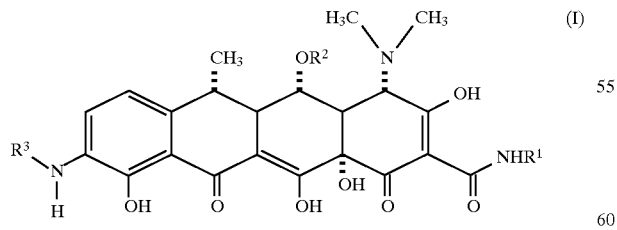

wherein $R^1$ is hydrogen or —CH$_2$NR$^5$R$^6$;
$R^2$ is $R^4$(CH$_2$)$_n$CO—;
n is an integer from 0 to 4;
$R^3$ is $R^8$(CH$_2$)$_m$CO— or $R^8$(CH$_2$)$_m$SO$_2$—;
m is an integer from 0 to 4;
and when n is 0, then either:

(a) $R^4$ is selected from hydrogen; amino; monosubstituted amino selected from straight or branched (C$_1$–C$_6$) alkylamino, cyclopropylamino, cyclobutylamino, benzylamino and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-(1,2,4-triazolyl); straight or branched (C$_1$–C$_4$)alkyl selected from methyl, ethyl, n-propyl, 1-methylethyl, n-butyl, 1-methylpropyl, 2-methylpropyl and 1,1-dimethylethyl; (C$_3$–C$_6$) cycloalkyl selected from cyclopropyl, cyclobutyl, cyclopentyl and cyclohexyl; substituted (C$_3$–C$_6$) cycloalkyl (substitution selected from (C$_1$–C$_3$)alkyl, cyano, amino and (C$_1$–C$_3$)acyl); (C$_6$–C$_{10}$)aryl selected from phenyl, a-naphthyl and β-naphthyl; substituted (C$_6$–C$_{10}$)aryl (substitution selected from halo, (C$_1$–C$_4$) alkoxy, trihalo(C$_1$–C$_3$)alkyl, nitro, amino, cyano, (C$_1$–C$_4$)alkoxycarbonyl, (C$_1$–C$_3$)alkylamino and carboxy); (C$_7$–C$_9$)aralkyl selected from benzyl, 1-phenylethyl, 2-phenylethyl and phenylpropyl; a-amino-(C$_1$–C$_4$)alkyl selected from aminomethyl, a-aminoethyl, a-aminopropyl and a-aminobutyl; carboxy(C$_2$–C$_4$)-alkylamino selected from aminoacetic acid, a-aminobutyric acid and a-aminopropionic acid and their optical isomers; (C$_7$–C$_9$)aralkylamino; (C$_1$–C$_4$)alkoxycarbonylamino substituted (C$_1$–C$_4$) alkyl, substitution selected from phenyl and p-hydroxyphenyl; a-hydroxy(C$_1$–C$_3$)alkyl selected from hydroxymethyl, a-hydroxyethyl, a-hydroxy-1-methylethyl and a-hydroxypropyl; a-mercaptopropyl; and halo-(C$_1$–C$_3$)alkyl; or (b) $R^4$ is selected from $Q^1$, $Q^2$ and $Q^3$, wherein $Q^1$ is a five membered aromatic or saturated ring containing one N, O, S or Se heteroatom optionally having a benzo or pyrido ring fused thereto;

$Q^2$ is a five membered aromatic ring containing two heteroatoms independently selected from N, O, S and Se and optionally having a benzo or pyrido ring fused thereto; and $Q^3$ is a five membered saturated ring containing one or two heteroatoms independently selected from N, O, S and Se and an adjacent appended O heteroatom; or (c) $R^4$ is a six membered aromatic ring containing from one to three heteroatoms independently selected from N, O, S and Se, or a six membered saturated ring containing one or two heteroatoms independently selected from N, O, S and Se and an adjacent appended O heteroatom; or (d) $R^4$ is selected from acetyl, propionyl; chloroacetyl; trifluoroacetyl; (C$_3$–C$_6$)cycloalkylcarbonyl; (C$_1$–C$_{10}$) aroyl selected from benzoyl and naphthoyl; halo substituted (C$_6$–C$_{10}$)aroyl; (C$_1$–C$_4$)alkylbenzoyl; and (heterocycle)carbonyl, wherein said heterocycle is selected from the group consisting of $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (e) $R^4$ is selected from (C$_1$–C$_4$)alkoxycarbonyl selected from methoxycarbonyl, ethoxycarbonyl, straight or branched propoxylcarbonyl, straight or branched butoxycarbonyl and allyloxycarbonyl; vinyl; and substituted vinyl; or (f) $R^4$ is selected from $(C_1-C_4)$alkoxy; $C_6$-aryloxy selected from phenoxy and substituted phenoxy (substitution selected from halo, $(C_1-C_4)$alkyl, nitro, cyano, thiol, amino, carboxy and di$(C_1-C_3)$ alkylamino); $(C_7-C_{10})$aralkyloxy; vinyloxy and substituted vinyloxy (substitution selected from $(C_1-C_4)$ alkyl, cyano, carboxy, and $(C_6-C_{10})$aryl selected from phenyl, a-naphthyl and β-naphthyl); $R^aR^b$ amino $(C_1-C_4)$alkoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$ wherein p is 2–6, or $R^aR^b$ is —$(CH_2)_2W(CH_2)_2$— wherein W is selected from —$N(C_1-C_3)$alkyl (straight or branched), —NH, —NOB (wherein B is selected from hydrogen and $(C_1-C_3)$alkyl), O and S; and $R^aR^b$aminoxy, wherein $R^aR^b$ is a straight or branched $(C_1-C_4)$alkyl selected from methyl, ethyl, n-propyl, 1-methylethyl, n-butyl, 1-methylpropyl, 2-methylpropyl, and 1,1-dimethylethyl, or $R^aR^b$ is $(CH_2)_p$ wherein p is 2–6, or $R^aR^b$ is —$(CH_2)_2W(CH_2)_2$— wherein W is selected from —$N(C_1-C_3)$alkyl (straight or branched), —NH, —NOB (wherein B is selected from hydrogen and $(C_1-C_3)$alkyl), O and S;

and when n is 1, 2, 3 or 4, then either:

(a) $R^4$ is selected from hydrogen; amino; straight or branched $(C_1-C_4)$alkyl selected from methyl, ethyl, n-propyl, 1-methylethyl, n-butyl, 1-methylpropyl, 2-methylpropyl and 1,1-dimethylethyl; $(C_3-C_6)$ cycloalkyl selected from cyclopropyl, cyclobutyl, cyclopentyl and cyclohexyl; substituted $(C_3-C_6)$ cycloalkyl group (substitution selected from $(C_1-C_3)$ alkyl, cyano, amino and $(C_1-C_3)$acyl); $(C_6-C_{10})$aryl selected from phenyl, a-naphthyl and β-naphthyl; substituted $(C_6-C_{10})$aryl (substitution selected from halo, $(C_1-C_4)$alkoxy, trihalo$(C_1-C_3)$alkyl, nitro, amino, cyano, $(C_1-C_4)$alkoxycarbonyl; $(C_1-C_3)$alkylamino and carboxy); $(C_7-C_9)$aralkyl; acetyl; propionyl; chloroacetyl; trichloroacetyl; $(C_6-C_{10})$aroyl; $(C_1-C_4)$ alkylbenzoyl; $(C_3-C_6)$cycloalkylcarbonyl; and (heterocycle)carbonyl, wherein the heterocycle moiety is selected from the group consisting of $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (b) $R^4$ is selected from $(C_1-C_4)$alkoxy; $C_6$-aryloxy selected from phenoxy and substituted phenoxy (substitution selected from halo, $(C_1-C_4)$alkyl, nitro, cyano, thiol, amino, carboxy and di$(C_1-C_3)$ alkylamino); $(C_7-C_{10})$aralkyloxy; $(C_1-C_3)$alkylthio selected from methylthio, ethylthio, propylthio and allylthio; $C_6$-arylthio selected from phenylthio and substituted phenylthio (substitution selected from halo, $(C_1-C_4)$alkyl, nitro, cyano, thiol, amino, carboxy and di$(C_1-C_3)$alkylamino); $C_6$-arylsulfonyl selected from phenylsulfonyl and substituted phenylsulfonyl (substitution selected from halo, $(C_1-C_4)$alkoxy, trihalo $(C_1-C_3)$alkyl, nitro, amino, cyano, $(C_1-C_4)$ alkoxycarbonyl, $(C_1-C_3)$alkylamino and carboxy); and $(C_7-C_8)$aralkylthio; or (c) $R^4$ is selected from $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (d) $R^4$ is selected from hydroxy; mercapto; mono- or di-straight or branched chain $(C_1-C_6)$alkylamino selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl and 1-methyl-1-ethylpropyl amino; $(C_2-C_5)$ azacycloalkyl; carboxy$(C_2-C_4)$alkylamino selected from aminoacetic acid, a-aminopropionic acid, a-aminobutyric acid and their optical isomers; a-hydroxy$(C_1-C_3)$alkyl selected from hydroxymethyl, a-hydroxyethyl, a-hydroxy-1-methylethyl and a-hydroxypropyl; halo$(C_1-C_3)$ alkyl; acetyl; propionyl; chloroacetyl; trifluoroacetyl; $(C_6-C_{10})$aroyl selected from benzoyl and naphthoyl; halo substituted $(C_6-C_{10})$ aroyl; $(C_1-C_4)$alkylbenzoyl; $(C_3-C_6)$ cycloalkylcarbonyl; and (heterocycle)carbonyl, wherein the heterocycle moiety is selected from $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (e) $R^4$ is selected from $(C_1-C_4)$alkoxycarbonylamino selected from tert-butoxycarbonylamino, allyloxycarbonylamino, methoxycarbonylamino, ethoxycarbonylamino and propoxycarbonylamino; $(C_1-C_4)$alkoxycarbonyl selected from methoxycarbonyl, ethoxycarbonyl, straight or branched propoxycarbonyl, and straight or branched butoxycarbonyl; allyloxycarbonyl; $R^aR^b$amino$(C_1-C_4)$ alkoxy, wherein $R^aR^b$ is straight or branched $(C_1-C_4)$ alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W(CH_2)_2$— wherein W is selected from —$N(C_1-C_3)$alkyl (straight or branched), —NH, —NOB (wherein B is selected from hydrogen and $(C_1-C_3)$alkyl), O and S; and $R^aR^b$aminoxy, wherein $R^aR^b$ is straight or branched $(C_1-C_4)$alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2 W(CH_2)_2$— wherein W is selected from —$N(C_1-C_3)$ alkyl (straight or branched), —NH, —NOB (wherein B is selected from hydrogen and $(C_1-C_3)$alkyl), O and S;

and when $R^3$ is $R^8(CH_2)_mCO$ and m is 0, then $R^8$ is independently selected from the same group of substitutents that $R^4$ is selected from when n is 0;

and when $R^3$ is $R^8(CH_2)_mCO$ and m is 1, 2, 3 or 4, then $R^8$ is independently selected from the same group of substitutents that $R^4$ is selected from when n is 1, 2, 3 or 4;

and when $R^3$ is $R^8(CH_2)_mSO_2$— and n is 0, then either:

(a) $R^8$ is selected from amino; monosubstituted amino selected from straight or branched $(C_1-C_6)$-alkylamino, cyclopylamino, cyclobutylamino, benzylamino and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-(1,2,4-triazolyl); straight or branched ($C_1$–$C_4$)alkyl selected from methyl, ethyl, n-propyl, 1-methylethyl, n-butyl, 1-methylpropyl, 2-methylpropyl and 1,1-dimethylethyl; ($C_3$–$C_6$) cycloalkyl selected from cyclopropyl, cyclobutyl, cyclopentyl and cyclohexyl; substituted ($C_3$–$C_6$) cycloalkyl (substitution selected from ($C_1$–$C_3$)alkyl, cyano, amino and ($C_1$–$C_3$)acyl); ($C_6$–$C_{10}$)aryl selected from phenyl, a-naphthyl and β-naphthyl; substituted ($C_6$–$C_{10}$)aryl (substitution selected from halo, ($C_1$–$C_4$) alkoxy, trihalo($C_1$–$C_3$)alkyl, nitro, amino, cyano, ($C_1$–$C_4$)alkoxycarbonyl, ($C_1$–$C_3$)alkylamino and carboxy); ($C_7$–$C_9$)aralkyl; and halo($C_1$–$C_3$)alkyl; or (b) $R^8$ is a heterocycle group selected from $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; $R^aR^b$amino($C_1$–$C_4$)alkoxy, wherein $R^aR^b$ is straight or branched ($C_1$–$C_4$)alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W$—$(CH_2)_2$—, wherein W is selected from —N($C_1$–$C_3$)alkyl (straight or branched), —NH, —NOB (wherein B is selected from hydrogen and ($C_1$–$C_3$)alkyl), O and S; and $R^aR^b$ aminoxy, wherein $R^aR^b$ is straight or branched ($C_1$–$C_4$)alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W$ $(CH_2)_2$— wherein W is selected from —N($C_1$–$C_3$)alkyl (straight or branched), —NH, —NOB (wherein B is selected from hydrogen or ($C_1$–$C_3$)alkyl), O and S, wherein $Q^1$, $Q^2$ and $Q^3$ are defined as above;

and when $R^3$ is $R^8(CH_2)_mSO_2$— and n is 1, 2, 3 or 4, then either:

(a) $R^8$ is selected from hydrogen; straight or branched ($C_1$–$C_4$)alkyl selected from methyl, ethyl, n-propyl, 1-methylethyl, n-butyl, 1-methylpropyl, 2-methylpropyl and 1,1-dimethylethyl; ($C_1$–$C_4$) carboxyalkyl; ($C_3$–$C_6$)cycloalkyl selected from cyclopropyl, cyclobutyl, cyclopentyl and cyclohexyl; substituted ($C_3$–$C_6$)cycloalkyl (substitution selected from ($C_1$–$C_3$)alkyl, cyano, amino and ($C_1$–$C_3$)acyl); ($C_6$–$C_{10}$)aryl selected from phenyl, a-naphthyl and β-naphthyl; substituted ($C_6$–$C_{10}$)aryl (substitution selected from halo, ($C_1$–$C_3$)alkoxy, trihalo($C_1$–$C_3$) alkyl, nitro, amino, cyano, ($C_1$–$C_4$)alkoxycarbonyl, ($C_1$–$C_3$)alkylamino and carboxy); ($C_7$–$C_9$)aralkyl; ($C_1$–$C_4$)alkoxy; $C_6$-aryloxy selected from phenoxy and substituted phenoxy (substitution selected from halo, ($C_1$–$C_3$)alkyl, nitro, cyano, thiol, amino, carboxy and di($C_1$–$C_3$)alkylamino); ($C_7$–$C_{10}$)aralkyloxy; $R^aR^b$amino($C_1$–$C_4$)alkoxy, wherein $R^aR^b$ is straight or branched ($C_1$–$C_4$)alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W(CH_2)_2$—, wherein W selected from —N($C_1$–$C_3$)alkyl (straight or branched), —NH, —NOB (wherein B is selected from hydrogen and ($C_1$–$C_3$)alkyl), O and S; and $R^aR^b$ aminoxy, wherein $R^aR^b$ is straight or branched ($C_1$–$C_4$)alkyl selected from methyl, ethyl, n-propyl, 1-methylethyl, n-butyl, 1-methylpropyl, and 2-methylpropyl, or $R^aR^b$ is $(CH_2)_p$, wherein p is 2–6, or $R^aR^b$ is —$(CH_2)_2W$ $(CH_2)_2$—, wherein W is selected from —N($C_1$–$C_3$) alkyl (straight or branched), —NH, —NOB (wherein B is selected from hydrogen and ($C_1$–$C_3$)alkyl), O and S; or (b) $R^8$ is selected from ($C_1$–$C_3$)alkylthio selected from methylthio, ethylthio and n-propylthio; $C_6$-arylthio selected from phenylthio and substituted phenylthio (substitution selected from halo, ($C_1$–$C_3$)alkyl, nitro, cyano, thiol, amino, carboxy and di($C_1$–$C_3$) alkylamino); ($C_7$–$C_8$)aralkylthio; and heterocycle groups selected from the group consisting of $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (c) $R^8$ is selected from hydroxy; mercapto; mono- or di- straight or branched ($C_1$–$C_6$)alkylamino group selected from methyl, ethyl, n-propyl, 1-methylethyl, n-butyl, 1-methylpropyl, 2-methylpropyl, 1,1-dimethylethyl, 2-methylbutyl, 1,1,-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl and 1-methyl-1-ethylpropyl amino; halo($C_1$–$C_3$)alkyl; acetyl; propionyl; chloroacetyl; trifluoroacetyl; ($C_6$–$C_{10}$)aroyl selected from benzoyl and naphthoyl; halo substituted ($C_6$–$C_{10}$)aroyl; ($C_1$–$C_4$)alkylbenzoyl; ($C_3$–$C_6$)cycloalkylcarbonyl; and (heterocycle) carbonyl, wherein the heterocycle moiety is selected from $Q^1$, $Q^2$, $Q^3$, six membered aromatic rings containing one to three heteroatoms independently selected from N, O, S and Se, and six membered saturated rings containing one or two heteroatoms independently selected from N, O, S and Se and an adjacent appended O heteroatom, wherein $Q^1$, $Q^2$ and $Q^3$ are defined as above; or (d) $R^8$ is selected from ($C_1$–$C_4$)alkoxycarbonyl selected from methoxycarbonyl, ethoxycarbonyl, straight or branched propoxycarbonyl, allyloxycarbonyl and straight or branched butoxycarbonyl; and $R^5$ and $R^6$ are independently selected from hydrogen; straight or branched ($C_1$–$C_3$)alkyl selected from methyl, ethyl, n-propyl and 1-methylethyl; ($C_6$–$C_{10}$) aryl selected from phenyl, a-naphthyl and β-naphthyl; ($C_7$–$C_9$)aralkyl; heterocycles selected from the group consisting of $Q^1$, $Q^2$, $Q^3$, six membered aromatic rings containing from one to three heteroatoms independently selected from N, O, S and Se, and six membered saturated rings containing one or two heteroatoms independently selected from N, O, S and Se and an adjacent appended O heteroatom; —$(CH_2)_kCOOR^7$ where k is 0–4 and $R^7$ is selected from hydrogen and straight or branched ($C_1$–$C_3$)alkyl selected from methyl, ethyl, n-propyl and 1-methylethyl; and ($C_6$–$C_{10}$)aryl selected from phenyl, a-naphthyl and β-naphthyl, wherein $Q^1$, $Q^2$ and $Q^3$ are defined as above;

or $R^5$ and $R^6$, taken together, are —$(CH_2)_2W(CH_2)_2$—, wherein W is selected from $(CH_2)_q$ wherein q is 0–1, —NH, —N($C_1$–$C_3$)alkyl (straight or branched), —N($C_1$–$C_4$)alkoxy, oxygen, sulfur and substituted congeners selected from (L or D)proline, ethyl(L or D)prolinate, morpholine, pyrrolidine and piperidine;

with the proviso that: (a) $R^5$ and $R^6$ can not both be hydrogen;

or a pharmaceutically acceptable salt of such compound.

2. A compound according to claim 1, wherein $R^3$ is $R^8(CH_2)_mCO-$.

3. A compound according to claim 1, wherein $R^3$ is $R^8(CH_2)_mSO_2-$.

4. A compound according to claim 1, wherein $R^2$ is $(C_1-C_6)$alkyl-$(C=O)-$, phenyl-$(C=O)-$ or phenylmethyl-$(C=O)-$.

5. A compound according to claim 2, wherein $R^3$ is $-(C=O)-CH_2-N(CH_3)_2$.

6. A compound according to claim 1, wherein $R^3$ is selected from the group consisting of formyl, acetyl, methoxyacetyl, acetyloxyacetyl, benzoyl, 4-methoxybenzoyl, 2-methylbenzoyl, 2-fluorobenzoyl, pentafluorobenzoyl, 3-trifluoromethylbenzoyl, 2-furanylcarbonyl, 2-thienylcarbonyl, 4-aminobenzoyl, aminocarbonyl, phenylsulfonyl, 4-chlorophenylsulfonyl, 3-nitrophenylsulfonyl, 2-thienylsulfonyl, 3-nitrophenylsulfonyl, 2-thienylsulfonyl, methanesulfonyl, phenylmethoxyacetyl, hydroxyacetyl, methylaminoacetyl, dimethylaminoacetyl, 4-bromo-1-oxobutyl, (4-dimethylamino)benzoyl, aminoacetyl, ethylsulfonyl, chloroacetyl, bromoacetyl, 2-bromo-1-oxopropyl, cyclopropylaminoacetyl, (2-methylpropyl)aminoacetyl, (butylmethyl)aminoacetyl and (phenylmethyl)aminoacetyl.

7. A pharmaceutical composition for treating or preventing a condition caused by a bacterial infection in a mammal, including a human, comprising an amount of a compound according to claim 1 that is effective in treating or preventing such condition, and a pharmaceutical acceptable carrier.

8. A method of treating or preventing a condition caused by a bacterial infection in a mammal, including a human, comprising administering to said mammal an amount of a compound according to claim 1 that is effective in treating or preventing such condition.

* * * * *